United States Patent [19]

Elia et al.

[11] Patent Number: 5,324,294
[45] Date of Patent: Jun. 28, 1994

[54] BONE AUGMENTATION METHOD AND APPARATUS

[75] Inventors: James P. Elia, Scottsdale, Ariz.; Jerry W. Bains, 9013 Red Lawrence Dr., Scottsdale, Ariz. 85377

[73] Assignees: Dental Marketing Specialists; Jerry W. Bains, both of Scottsdale, Ariz.; a part interest

[21] Appl. No.: 961,474

[22] Filed: Oct. 15, 1992

[51] Int. Cl.⁵ .............................. A61B 17/56
[52] U.S. Cl. ........................................ 606/76
[58] Field of Search .............. 606/61, 72, 73, 77, 606/78; 623/13, 17

[56] References Cited

U.S. PATENT DOCUMENTS

| | | | |
|---|---|---|---|
| 3,085,569 | 4/1963 | Cook | 602/9 |
| 3,577,837 | 5/1971 | Bader | 623/13 |
| 4,759,765 | 7/1988 | Van Kampen | 606/77 |
| 4,834,752 | 5/1989 | Van Kampen | 623/13 |
| 4,960,420 | 10/1990 | Goble | 606/77 |
| 5,002,576 | 3/1991 | Fuhrmann | 623/17 |
| 5,035,716 | 7/1991 | Downey | 623/17 |

Primary Examiner—Michael A. Brown
Attorney, Agent, or Firm—Tod R. Nissle

[57] ABSTRACT

A method and apparatus for anchoring flaps of tissue in the body utilizes panels of material including a plurality of outwardly extending quills, or pins, to engage and secure the flaps of tissue in place.

5 Claims, 10 Drawing Sheets

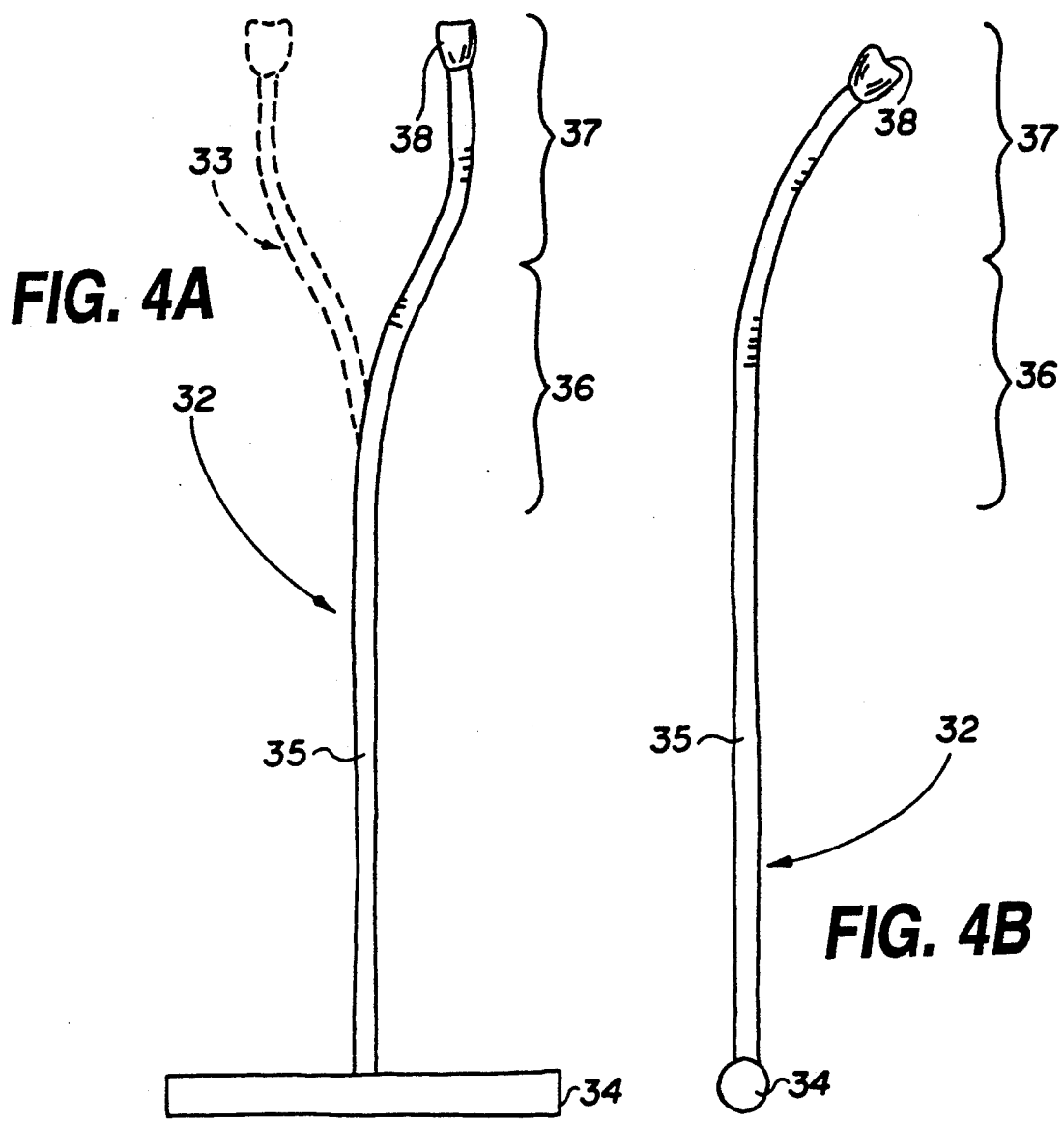
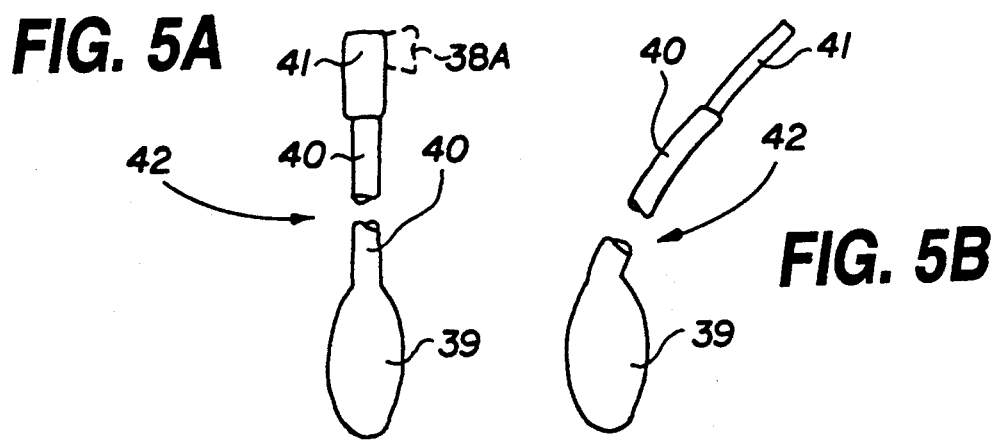

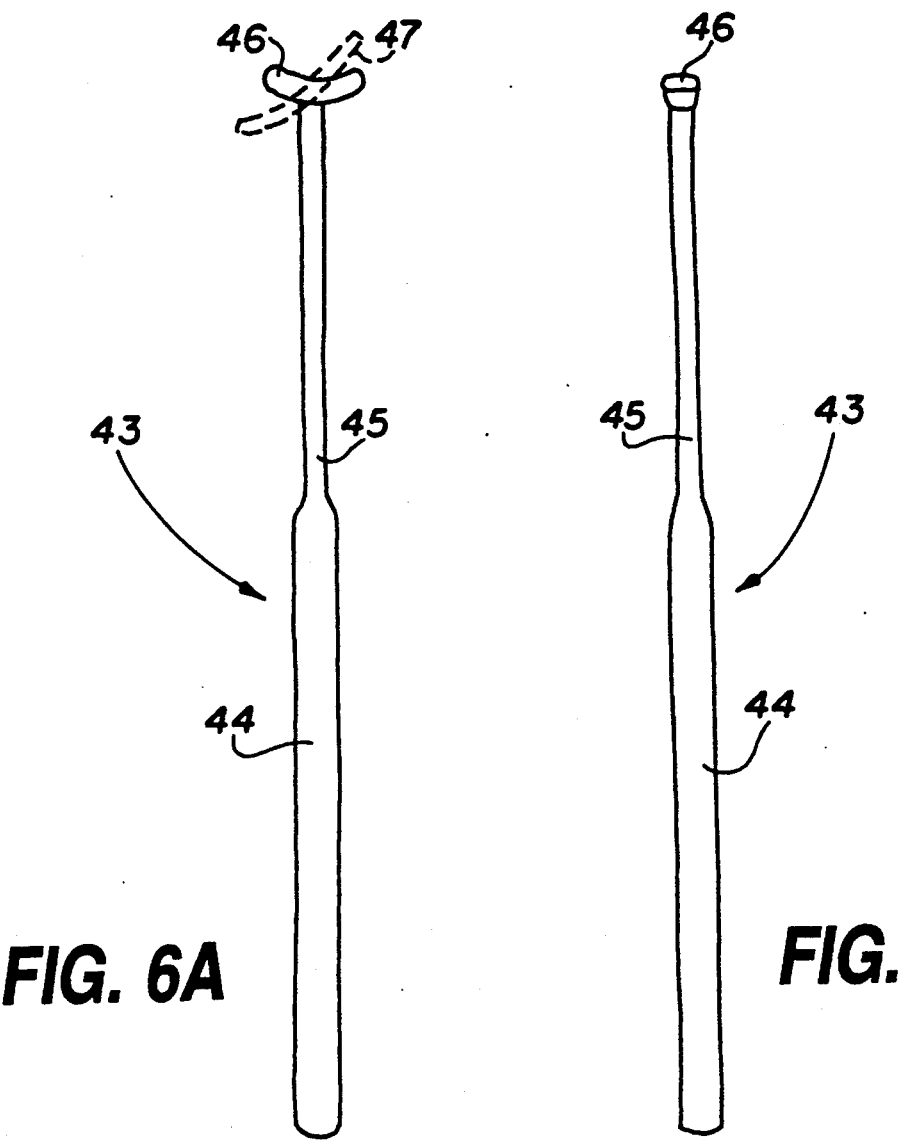

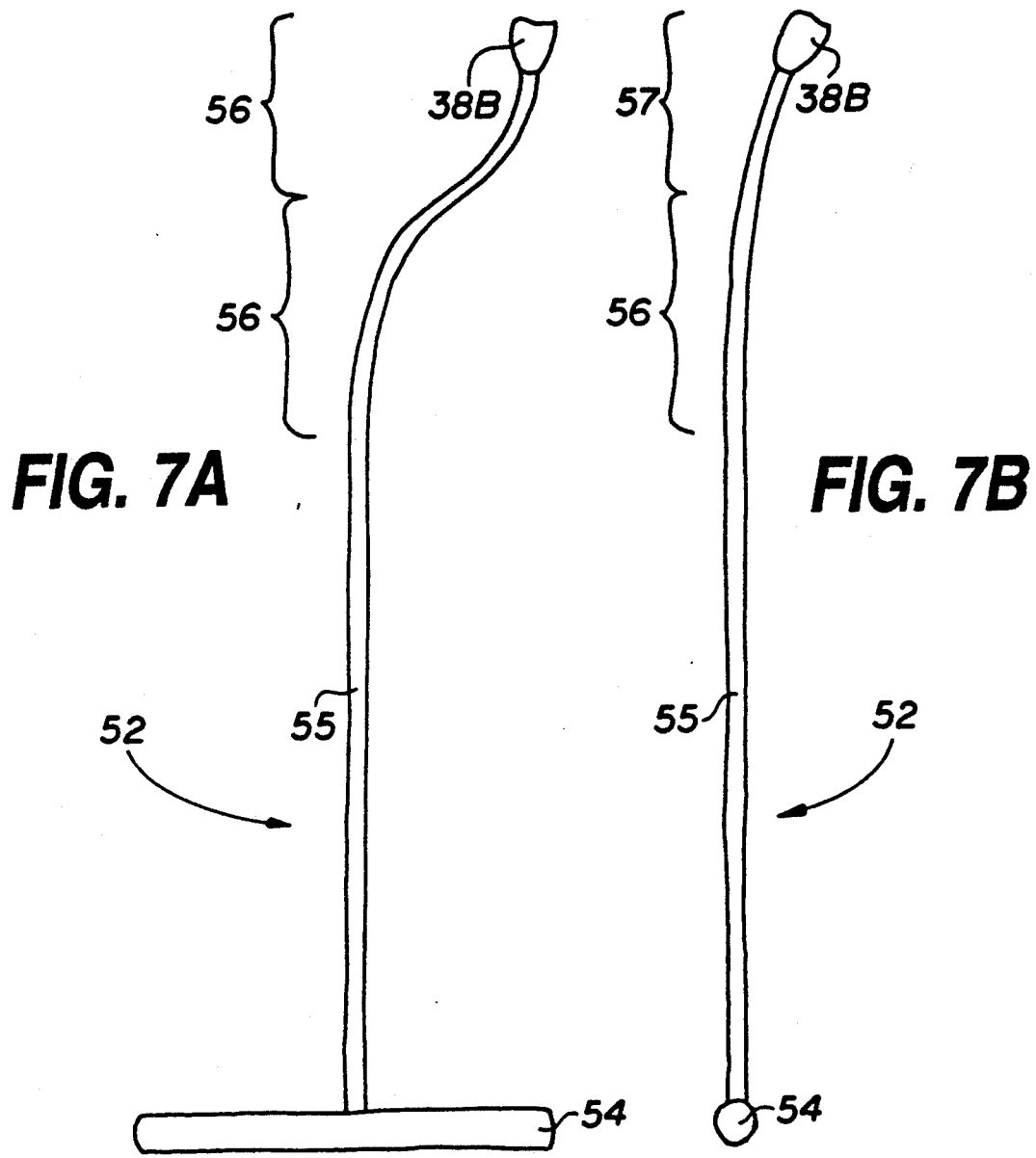

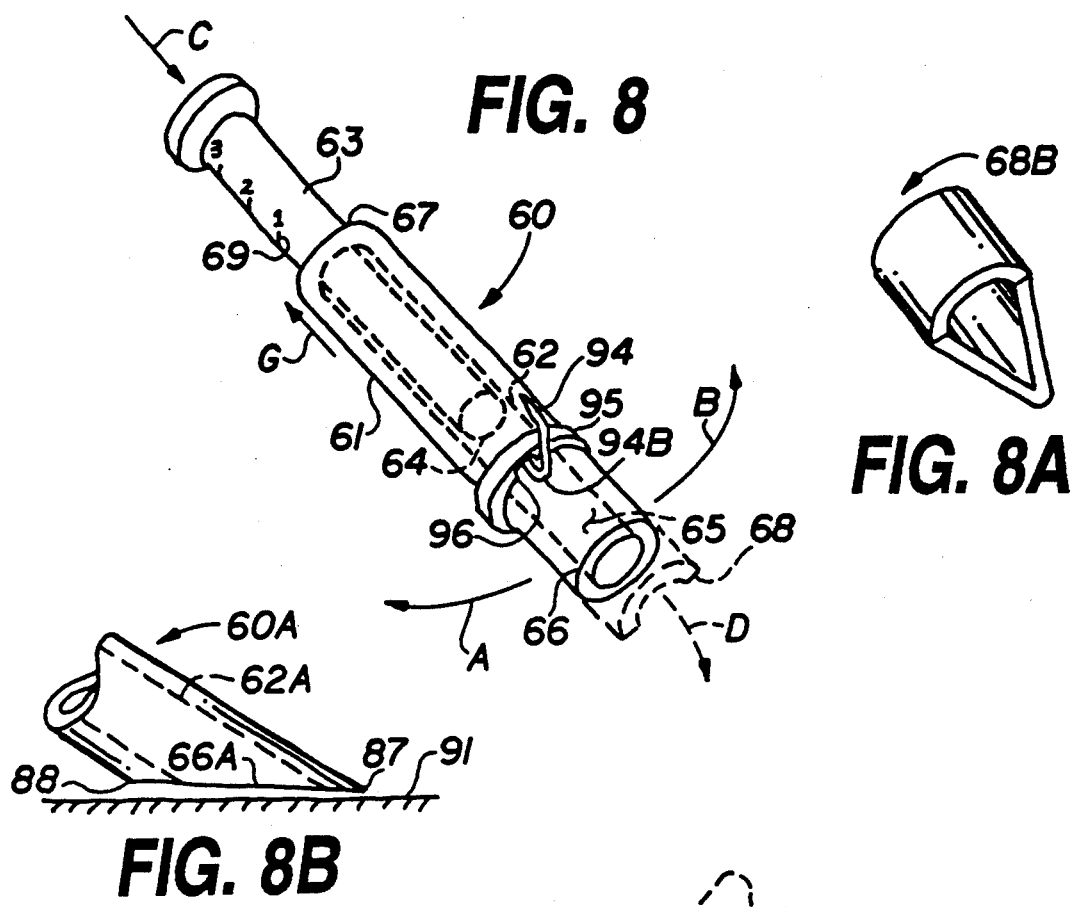
FIG. 8
FIG. 8A
FIG. 8B
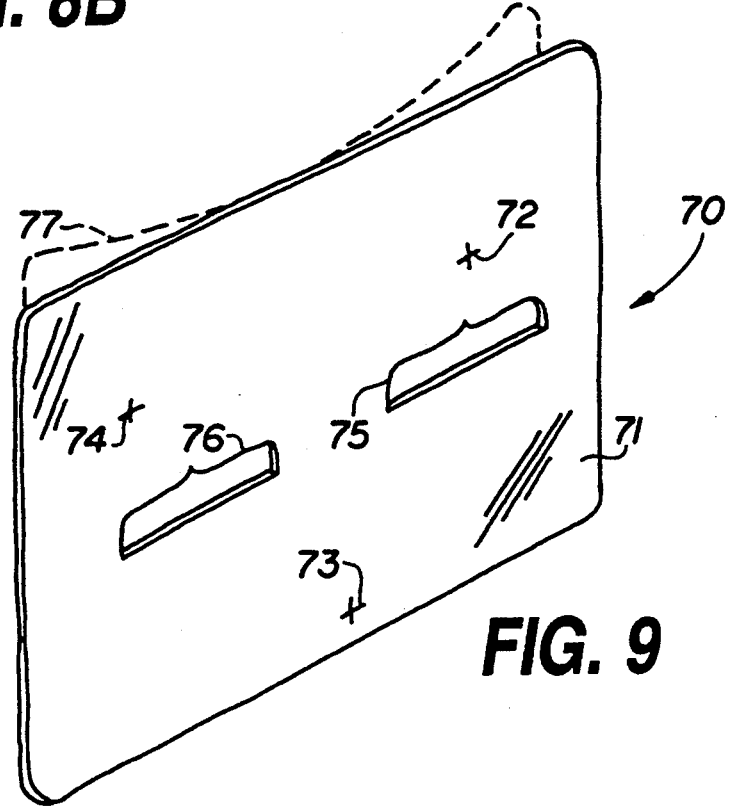
FIG. 9

BONE AUGMENTATION METHOD AND APPARATUS

This invention relates to a method and apparatus for augmenting the bone in the face of a human being.

More particularly, the invention relates to medical instruments which can be inserted through an intraoral incision and use to pack bone augmentation material against the bone underlying facial tissue.

In a further respect, the invention relates to a pliable syringe which can be inserted through an intraoral incision intermediate facial tissue and underlying bone and be shaped to conform to the curvature of the face to deliver bone augmentation material at a selected point intermediate facial tissue and underlying bone.

In another respect, the invention relates to a template which can be placed over the face in registration with landmarks on the face to identify specific facial areas in which the underlying bone is to be augmented.

In still a further respect, the invention relates to a containment member which can be inserted through an intraoral incision to a position intermediate facial tissue and the bone to receive and prevent the migration of bone augmentation material.

In yet another respect, the invention relates to a method of augmenting the bone structure of the face of a human being by inserting a containment member through an intraoral incision to a position intermediate facial tissue and underlying bone and by packing bone augmentation material into the containment member.

The augmentation of the bone structure of the face for the purpose of replacing or repairing abnormal bone structure or the purpose of altering the cosmetic appearance of the face is well known. Conventional augmentation procedures typically have several disadvantages. First, silicon implants are often utilized to cosmetically alter the appearance of an individual. Such implants are prone to leak, as has recently been well documented in the press with respect to breast implants. Second, augmentation of the bone structure of the face often requires that an incision be made and a portion of the facial tissue be peeled away from the underlying bone structure. The wholesale peeling of skin away from the skull increases the risk of infection and the morbidity. Third, molding an implant or bone augmentation material to a desired contour is often impeded because the implant or material used has a specific fixed shape. Fourth, attempting to utilize hydroxyapatite powder or other similar moldable bone augmentation material is difficult because the bone augmentation material tends to migrate from the site at which the material is initially inserted intermediate the facial tissue and underlying bone structure. Fifth, molding hydroxyapatite powder or other potentially moldable material is difficult because once the moldable materials is inserted intermediate facial tissue and underlying bone, there is no convenient way to mold the material without externally displacing facial tissue. Sixth, silicon and other similar implant material cannot be resorbed by the body.

Accordingly, it would be highly desirable to provide an improved method and apparatus which permitted augmentation of the bone structure of the face, which did not require an incision distant from the site to be augmented or require the subsequent peeling of facial tissue from the skull, which enabled bone augmentation materials to be readily molded, which prevented migration of bone augmentation materials, and which enabled resorbable materials to be utilized during augmentation of the bone structure of the face.

Therefore, it is a principal object of the invention to provide an improved method and apparatus for augmenting the bone structure of the face.

A further object of the invention is to provide an improved method and apparatus which permits augmentation of the bone structure of the face to be accomplished through a small intraoral incision without requiring that facial tissue be peeled away from the skull and exposed to the open air.

Another object of the instant invention is to provide an improved syringe which delivers bone augmentation material intermediate facial tissue and underlying bone and which can conform to the curvatures in the facial bone structure.

Still a further object of the invention is to provide apparatus for containing moldable bone augmentation material at a selected location intermediate facial tissue and underlying bone to prevent migration of the bone augmentation material.

Yet another object of the invention is to provide a medical instrument which can be inserted through an intraoral incision and utilized to pack bone augmentation material at a selected site intermediate facial tissue and underlying bone.

These and other, further and more specific objects and advantages of the invention will be apparent to those skilled in the art from the following detailed description thereof, taken in conjunction with the drawings in which:

FIG. 4A is a top view illustrating a medical instrument used in the practice of the invention;

FIG. 4B is a side view of the medical instrument of FIG. 4A;

FIG. 5A is a top view illustrating a medical instrument used in the practice of the invention;

FIG. 5B is a side view of the packing tip of the medical instrument of FIG. 5A;

FIG. 6A is a top view illustrating a medical instrument used in the practice of the invention;

FIG. 6B is a side view of the medical instrument of FIG. 6A;

FIG. 7A is a top view illustrating a medical instrument used in the practice of the invention;

FIG. 7B is a side view of the medical instrument of FIG. 7A;

FIG. 8 is a perspective view illustrating a flexible syringe used in the practice of the invention;

FIG. 8A is an alternate embodiment of the tip of the syringe shown in FIG. 8.

FIG. 8B shows the plunger with a beveled end.

FIG. 9 is a perspective view illustrating a template used in the invention;

Figure 1:
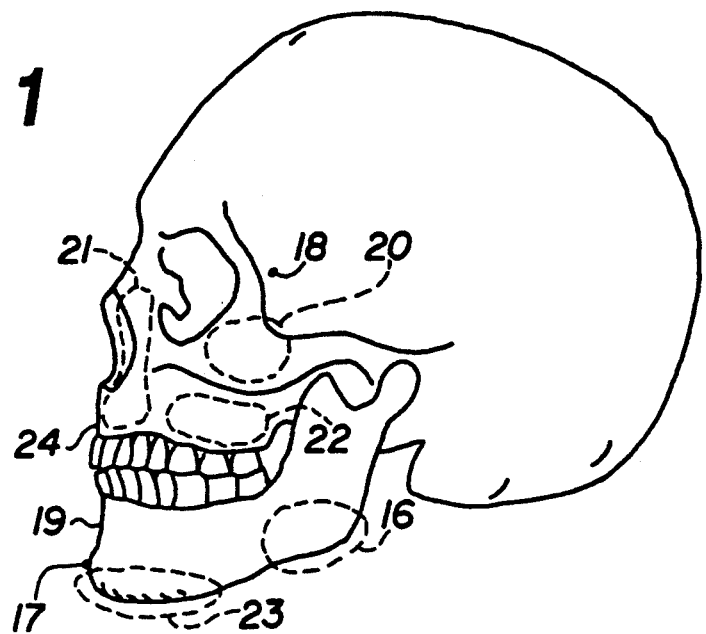
FIG. 1 is a side view illustrating the skull of a human being and indicating general areas in which the skull bone structure is often augmented.

Briefly, in accordance with our invention, we provide an improved medical instrument for insertion through an intraoral incision at the front of the mouth to pack bone augmenting material intermediate facial tissue and underlying bone at one side of the face. The medical instrument includes a handle; a proximate end attached to the handle; a mediate portion attached to the proximate end and shaped to curve from the front of the face around a selected portion of facial bone to a selected treatment area; and, a distal end attached to the mediate portion and shaped to curve inwardly toward the treatment area and to compress the bone augmenting material toward underlying bone in the target area.

In another embodiment of our invention, we provide a medical instrument for insertion through an intraoral incision at the front of the mouth to pack bone augmenting material intermediate facial tissue and the paranasal bone of the face. The medical instrument includes a handle; a mediate portion attached to the handle and shaped to extend through the intraoral incision to the paranasal bone; and, an arcuate distal end attached to the mediate portion for packing bone augmenting material and shaped to conform to the paranasal bone.

In a further embodiment of our invention, we provide a medical instrument for insertion through an intraoral incision at the front of the mouth to pack bone augmenting material intermediate facial tissue and the submental bone of the face. The medical instrument includes a handle; a mediate portion attached to the handle and shaped to extend through the intraoral incision to the submental bone; and, a paddle shaped distal end attached to the mediate portion for packing bone augmenting material and shaped to compress the bone augmenting material against the submental bone.

In still another embodiment of our invention, we provide a syringe assembly for insertion through an intraoral incision at the front of the mouth to inject bone augmenting material intermediate facial tissue and underlying bone. The syringe assembly includes a hollow elongate pliable housing having a first end and a second end for dispensing bone augmenting material; a plunger having a distal end extending past the first end into and partially along the housing and spaced apart from the second end, the distal end sealingly engaging the housing; and, a quantity of bone augmenting material stored in the housing intermediate the distal end of the plunger and the second end. The bone augmenting material is forced out of the second end when the plunger is pressed into the housing such that the distal end moves toward the first end of the housing.

In yet a further embodiment of the invention, we provide a template for use in inserting bone augmenting material intermediate facial tissue and underlying bone. The template includes a panel member including a first topographical reference point corresponding to a first selected landmark on the face of a human being; a second topographical reference point corresponding to a second selected landmark on the face of a human being; and, an aperture formed through the panel member and circumscribing a selected area on the face of a human being when the panel member is placed adjacent the face and the first topographical point is in registration with the first selected landmark and the second topographical point is in registration with the second selected landmark.

In yet still a further embodiment of the invention, we provide a containment member for insertion through an intraoral incision to a position intermediate facial tissue and underlying bone. The containment member is shaped to receive bone augmenting material and store the bone augmenting material adjacent the underlying bone. The containment member comprises a pocket for receiving bone augmenting material. The pocket includes a sheet which extends intermediate facial tissue and underlying bone when the containment member is inserted between facial tissue and underlying bone.

In a further embodiment of the invention, we provide a method for augmenting the bone structure of the face of a human being. The method comprises the steps of making an intraoral incision; inserting an instrument through the incision to separate facial tissue from underlying bone structure until a selected treatment area in the face is reached; inserting a containment member through the intraoral incision and intermediate the separated facial tissue and underlying bone structure to said selected treatment area; and, inserting bone augmenting material in the containment member adjacent the underlying bone structure in the treatment area.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates the zygomatic 20, molar 22, paranasal 21 and submental 23 bone areas on one side of the face of the skull of a human being. The submalar bone area on each side of the face extends from the molar area 22 upwardly under the cheek bone. The molar area 22 includes the maxillary bone. One embodiment of the invention deposits bone augmentation material on or adjacent the maxillary bone to alter the contour of the facial tissue comprising the cheek of a patient.

Figure 2:
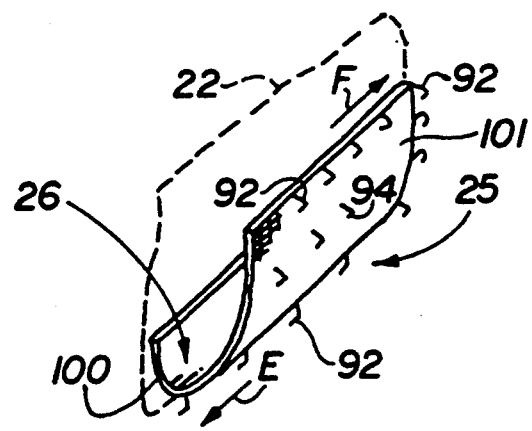
FIG. 2 is a perspective view illustrating a pocket used in accordance with the invention to receive and contain bone augmentation material.

FIG. 2 illustrates a J-shaped containment integument or pocket 25 formed from a sheet of collagen, polyglycolic acid or other suitable material. The pocket 25 is preferably, but not necessarily, somewhat pliable and can, if desired, be sufficiently stiff to retain its form when inserted between, for example, the molar bone area 22 (FIG. 2) and facial tissue (not shown in FIG. 2.). Hydroxyapatite or other bone augmentation material is inserted in the lower cupped portion 100 of pocket 25 in the direction indicated by arrow 26 in FIG. 2. Pocket 25 is presently preferably positioned intermediate facial tissue and underlying bone by inserting pocket 25 through an intraoral incision. If desired, pocket 25 can be inserted intermediate facial tissue and underlying bone after an incision is made and facial tissue is peeled away from the underlying bone in the same manner that a protective backing is peeled off of the adhesive on the back of a label. The lower cupped portion 100 of pocket 25 can be stiffer or thicker than the upper portion 101 to facilitate the retention by portion 100 of its shape after hydroxyapatite or other bone augmentation material is inserted in portion 100.

Figure 12:
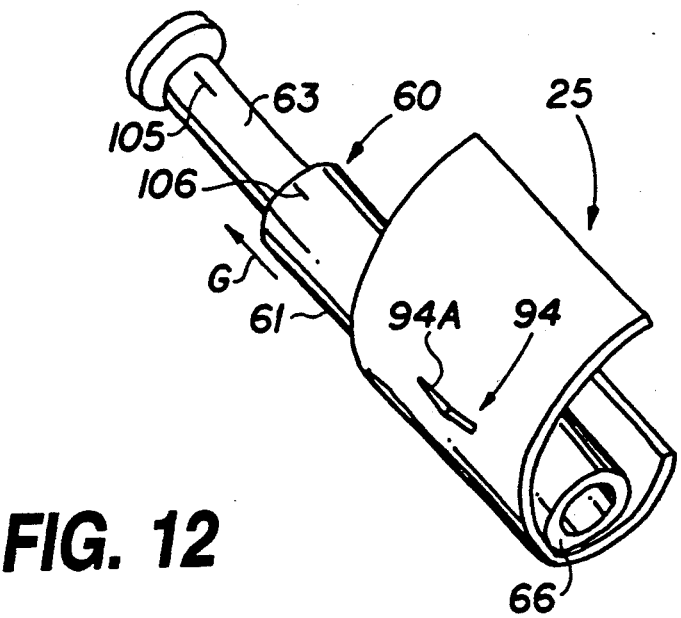
FIG. 12 is a perspective view illustrating a syringe adapted to insert a containment system constructed in accordance with the invention.

Pocket 25 can, if desired, be provided with one or more hooks or staples 92, 94 which outwardly extend from pocket 25 to engage facial or other bodily tissue. The distal ends of staples 92, 94 are formed in a manner similar to a fish hook such that once the distal ends penetrate tissue they are not readily removed. In use of the pocket of FIG. 2, the pocket is inserted intermediate facial tissue and bone in the direction of arrow F and is then pulled gently in the direction of arrow E to cause the distal ends of hooks 92, 94 to engage facial tissue and hold pocket 25 in place. After hooks 92, 94 anchor pocket 25 in position, hydroxyapatite or other bone augmentation material is inserted in the lower portion 100 in the direction indicated by arrow 26. When pocket 25 is provided with hooks 92, 94, it is crucial that the pocket 25 be inserted in the proper orientation intermediate facial tissue and underlying bone. When the orientation indicia 105 and 106 in FIG. 12 point upwardly toward the sky, and when a patient is seated in an upright position, then the surgeon knows that the pocket 25 in FIG. 12 is being inserted with the mouth of the pocket opening upwardly toward the sky. It is, as would be appreciated by those of skill in the art, important to have the mouth of pocket 25 opening upwardly so that when bone augmentation material is deposited in the cupped portion 100 of pocket 25 and can not be pulled downwardly and caused to migrate under the force of gravity. Migration of the bone augmentation material occurs when the augmentation material moves intermediate facial tissue and underlying bone to sites other than the site at which the augmentation material was originally deposited by the surgeon.

Figure 3:
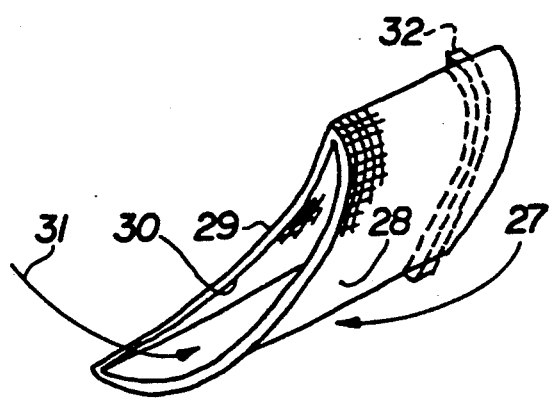
FIG. 3 is a perspective view illustrating another pocket used in the invention to receive and contain bone augmentation material.

FIG. 3 illustrates another containment pocket or sock 27 formed from a pair of sheets 28, 29 of collagen or other material. Each sheet 28, 29 can be provided with one or more stiffening ribs 32. Hydroxyapatite or other bone augmentation material is inserted in sock 26 intermediate sheets 28, 29 in the manner indicated by arrow 31 in FIG. 3.

The outer surfaces of pockets 25 and 26 can be provided with small hooks, with adhesive, or with other means which engages facial tissue and underlying bone and anchors pockets 25 and 26 in a desired position intermediate facial tissue and underlying bone. Pockets 25 and 26 can be sutured or otherwise affixed to facial tissue or underlying bone.

FIGS. 4A and 4B illustrate a medical instrument 32 used to pack bone augmentation material in the molar 22 and submalar bone areas of the left side (FIG. 1) of the face of an individual. The submalar bone area includes the maxillary bone and extends beneath the cheek bone. The instrument 33 used to pack bone augmentation material in the molar area 22 of the right side of the face of an individual is, as would be appreciated by one of skill in the art, the mirror image of instrument 32. Instrument 32 includes handle 34, proximate end 35 attached to handle 34, mediate portion 36 attached to end 35, and distal end 37 attached to mediate portion 36. Portion 36 is shaped and dimensioned to extend around the skull from about point 24 or another selected point at the front of the upper jaw of the face and to extend toward the molar 22 and submalar areas. End 37 is shaped to extend inwardly toward the molar area 22 and to compress bone augmentation material toward and against bone in molar area 22. While a segment of portion 36 can, if desired, be straight, in FIG. 4A portion 36 is curved along substantially its entire length. Portion 37 can, if desired, be straight or curved along its entire length. In FIG. 4A portion 37 is, however, curved along about half of its length. Tip 38 on distal end 37 has a generally conical shape in FIGS. 4A and 4B, but can be paddle shaped or take on any other shape which facilitates compacting of bone augmentation material. Portion 36 extends along a line which defines a first curve in three dimensional space. Portion 37 extends along a line which defines a second curve in three dimensional space. Portion 36 does not lie in a single flat plane. Portion 37 does not lie in a single flat plane. The first curve "opens" in a different direction (to the lower right of portion 36 in FIG. 1) than does the second curve. The second curve opens to the upper left of instrument 32 in FIG. 4A. The first curve bends to the right in FIG. 4A, while the second curve bends to the left. The first and second curves normally can not be superimposed upon one another, regardless of their orientation. While the curvature of the first curve and second curve can be equivalent, the curvature of the first curve ordinarily differs from the curvature of the second curve.

FIGS. 5A and 5B illustrate a medical instrument 42 used to pack bone augmentation material in the submental area 23 of the chin (FIG. 1) of the face of an individual. The instrument 42 includes handle 39, mediate portion 40 attached to handle 39, and paddle shaped distal end 41 attached to mediate portion 40. End 41 is used to pack bone augmentation material against the submental bone. Paddle 41 can also include or be replaced by a cone shaped compactor member as indicated by dashed lines 38A in FIG. 5A.

FIGS. 6A and 6B illustrate a medical instrument 43 used to pack bone augmentation material in the paranasal area 21 (FIG. 1) of the face of an individual. The instrument 43 includes a handle 44, a mediate portion 45 attached to handle 44, and an arcuate or stirrup shaped distal end 46 attached to mediate portion 45. End 46 is shaped to generally conform to the convex shape of the outer surface of the paranasal bone area 21. The length, curvature, and orientation of end 46 can be altered as desired. In FIG. 6A, dashed lines 47 indicate another possible shape and orientation of end 46.

FIGS. 7A and 7B illustrate a medical instrument 52 used to pack bone augmentation material in the zygomatic area 20 of the left side (FIG. 1) of the face of an individual. The instrument used to pack bone augmentation material in the zygomatic area 20 of the right side of the face of an individual is, as would be appreciated by one of skill in the art, the mirror image of instrument 52. Instrument 52 includes handle 54, proximate end 55 attached to handle 54, mediate portion 56 attached to end 55, and distal end 57 attached to mediate portion 56. Portion 56 is shaped and dimensioned to extend around the skull from about point 24 or another selected point at the front of the upper jaw of the face and to extend toward the zygomatic area 20. While a segment of portion 56 can, if desired, be straight, in FIG. 7A portion 56 is curved along its entire length. End 57 is shaped to extend inwardly toward the zygomatic area 20 and to compress bone augmentation material toward and against bone in zygomatic area 20. While all or a segment of portion 57 can, if desired, be straight, in FIG. 7A portion 57 is curved along substantially its entire length. Tip 38B on distal end 57 has a generally conical shape in FIGS. 6A and 6B, but can be paddle shaped or take on any other shape which facilitates compacting of bone augmentation material. Portion 56 extends along a line which defines a first curve in three dimensional space. Portion 57 extends along a line which defines a second curve in three dimensional space. Portion 56 does not lie in a single flat plane. Portion 57 does not lie in a single flat plane. The first curve "opens" in a different direction (to the lower right of portion 56 in FIG. 1) than does the second curve. The second curve opens to the upper left of instrument 52 in FIG. 7A. The first curve bends to the right in FIG. 7A, while the second curve bends to the left. The first and second curves normally can not be superimposed upon one another, regardless of their orientation. While the curvature of the first curve and second curve can be equivalent, the curvature of the first curve ordinarily differs from the curvature of the second curve.

Figure 10A:
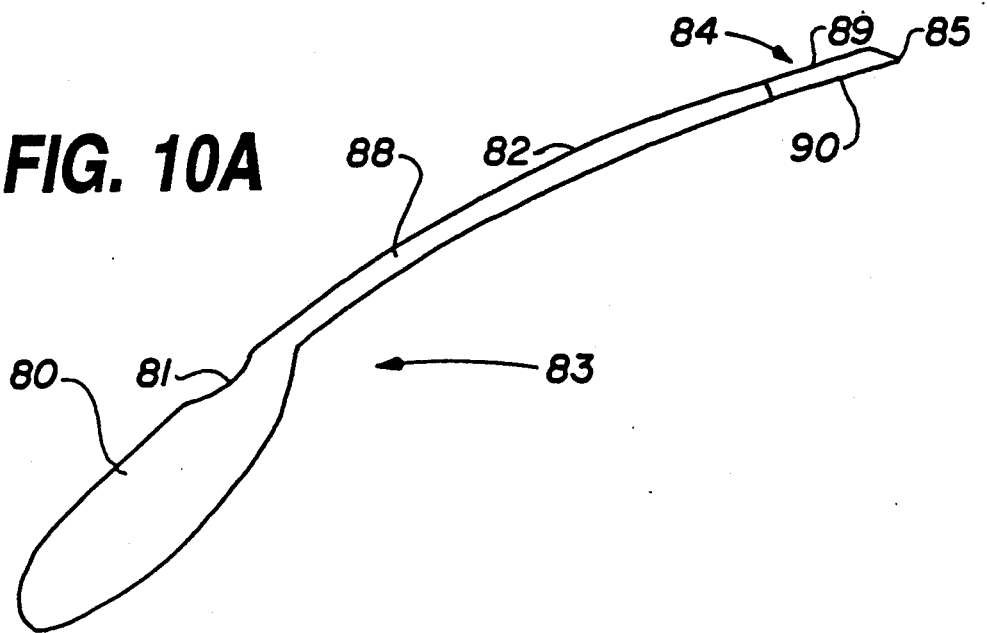
FIG. 10A is a side view illustrating a medical instrument used in the practice of the invention.
Figure 10B:
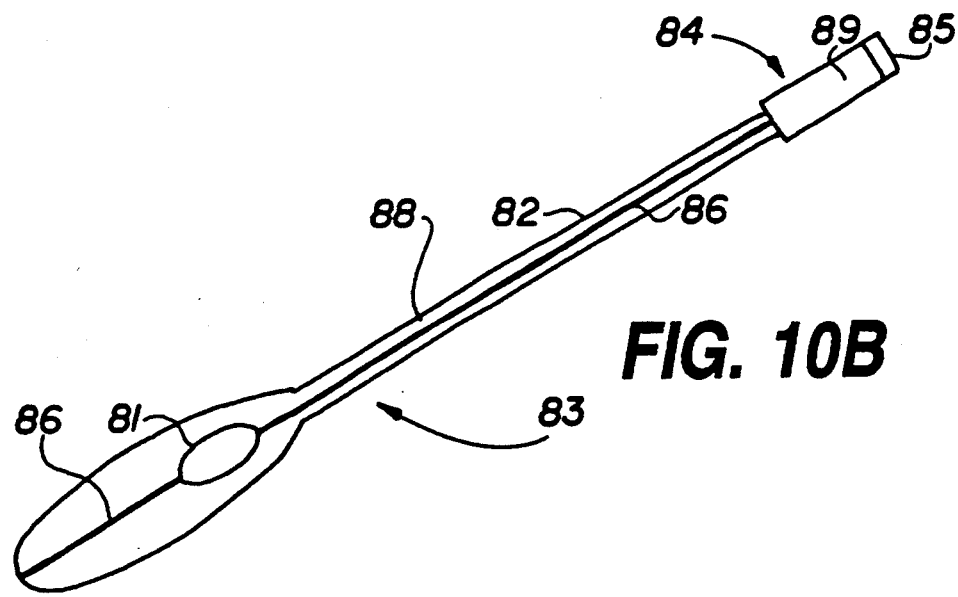
FIG. 10B is a top view illustrating the medical instrument of FIG. 10A.

FIGS. 10A and 10B also illustrate a medical instrument 83 used to pack bone augmentation material in the zygomatic area 20 of the left or right side of the face of an individual. The instrument 83 includes a handle 80, proximate end 88 attached to handle 80, mediate portion 82 attached to end 88, and distal end or paddle 84 attached to mediate portion 82. Portion 82 is shaped and dimensioned to curve around the skull from a point at the front of the upper jaw of the face and to extend to the zygomatic area 20. End 84 is also shaped to curve inwardly toward the zygomatic area 20 and to compress bone augmentation material toward and against bone in the zygomatic area 20. End 84 is provided with a sharp leading edge which can be used to separate facial tissue from underlying bone after an intraoral incision is formed. In use of instrument 83, bottom surface 90 of end 84 normally faces and is adjacent bone structure in the face, while upper surface 89 of end 84 normally is adjacent facial tissue and faces outwardly from the skull and from bone which is beneath end 84. Thumbrest 81 is provided on top of handle 80. Reference line 86 is inscribed along the top of instrument 83. In use of the instrument 83, the reference line 86 normally faces outwardly from the patient's face. Line 86 enables a surgeon to visually determine the orientation of end 84 after end 84 has been inserted through an intraoral incision and intermediate facial tissue and underlying bone. When end B4 and portion B2 are inserted intermediate facial tissue and underlying bone, portion 82 and end 84 are covered by facial tissue and can not seen by the surgeon. Reference lines or marks similar to line 86 can be inscribed on the instruments illustrated in FIGS. 4A, 5A, 6A, and 7A, and can also be inscribed on the plunger 63 of the syringe assembly 60 depicted in FIG. 8.

The syringe assembly 60 illustrated in FIG. 8 includes a hollow elongate pliable housing 61 with a first end 67 and a second end 66 for dispensing bone augmentation material. Plunger 63 includes a distal end 64 extending past first end 67 partially into the housing 61. End 64 is spaced apart from second end 66. End 64 sealingly engages the inner cylindrical wall 62 of housing 61. A quantity of bone augmentation material and/or soft tissue augmentation material (not shown) is stored in cylindrical open area 65 inside housing 61. When plunger 63 is depressed in the direction of arrow C, bone augmentation material and/or soft tissue augmentation material is forced out of end 66. End 66 can be provided with a semi-cylindrical tip 68 or other tip which tends to cause augmentation material flowing from end 66 to flow downwardly in the direction of arrow D. Both housing 61 and plunger 63 are pliable such that housing 61 and plunger 63 can be readily bent in any direction in the manner indicated by arrows A and B in FIG. 8. Further, housing 61 and plunger 63 are preferably made from elastic materials which will, after housing 61 is bent into a certain shape, permit housing 61 to hold the shape for at least a short period of time and will permit housing 61 to hold its shape while plunger 63 is depressed in the direction of arrow C. Graduations 69 can be provided on plunger 63 to indicate the quantity of bone augmentation material which has been extruded from end 66. Tip 68 or end 66 can, in part or in whole, be fabricated from metal. When housing 60 and plunger 63 are fabricated from teflon, rubber, plastic, or some other material which tends to dampen vibrations, it is preferred that the portions of end 55 and tip 68 which normally contact bone be comprised of or covered by metal. When the metal contacts and is moved over bone, the scratching of the metal on the bone produces a scratching sound and/or vibrations which can be heard by the surgeon and/or detected by the sense of touch in the surgeon's fingers which are grasping the syringe assembly. The ability to detect the proximity of the tip 68 of the syringe assembly to underlying bone is important because it helps to prevent the surgeon's injecting bone augmentation materials at locations spaced away from the bone. Vibrations emanating from a metal tip 68 can be transmitted through a housing even when the housing is fabricated from plastic, rubber, or glass. An alternate embodiment of tip 68B is illustrated in FIG. 8A.

The end 66 of plunger 60 can, instead of being "squared off" in the manner illustrated in FIG. 8, be beveled as shown in FIG. 8B. The beveled end of plunger 60A in FIG. 8B includes tip 87, circular end 66A, cylindrical aperture 62A, and lower edge or point 88. When the beveled end of plunger 60A moves over underlying bone 91, either point 88 or tip 87 ordinarily contacts bone 91. Consequently, either point 88 or tip 87 are fabricated from metal, or, a metal clip, sleeve, or other member is attached to at least point 88 and tip 87 of the beveled end of plunger 60A such that the metal member contacts bone 91 and generates the scratching sound or noise referred to above.

Figure 11:
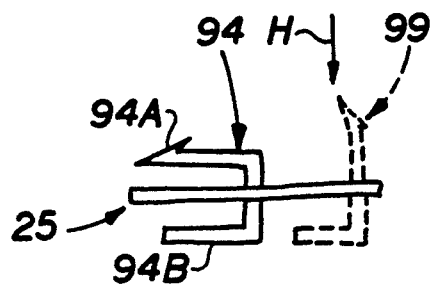
FIG. 11 is a side elevation view illustrating a staple or hook used in a containment system constructed in accordance with the principles of the invention.

Housing 61 can, if desired, include one or more rings 95 fixedly attached thereto with a cylindrical aperture 96 formed in ring 95 such that one end 94B of a staple 94 can be slidably inserted in aperture 96 in the manner illustrated in FIG. 8. The intermediate portion of staple 94 is fixedly secured in pocket 25 in the manner illustrated in FIGS. 2, 11, and 12. Pocket 25 is not included in FIG. 8 for the sake of clarity. Consequently, when end 94B is slidably inserted in aperture 96, pocket 25 is positioned about housing 61 in the manner shown in FIG. 12. After housing 61 is inserted to a desired position intermediate facial tissue and bone, the syringe is pulled in the direction of arrow G, causing the distal end 94A of staple 94 to penetrate facial tissue, end 94B to slide free from aperture 96, housing 61 to slide out of pocket 25, and pocket 25 to be anchored in place intermediate facial tissue and underlying bone. The syringe plunger 63 is then depressed to dispense hydroxyapatite or other material from end 66 of housing 61 into pocket 25 in the direction indicated by arrow 26 in FIG. 2. The end of the syringe can be used to pack the bone augmentation material in place in pocket 25.

Pocket 25 can be provided with hooks 99 having distal ends which extend outwardly from and are generally perpendicular to pocket 25. Such hooks 99 are desirable in the event it is intended to compress facial tissue against pocket 25 in the direction of arrow H. If a sufficient number of hooks 99 are utilized in this fashion, facial tissue can be pressed and anchored against pocket 25 by hooks 99 in a fashion which may eliminate or reduce the need for sutures. Pocket 25 can be inserted intermediate facial tissue and underlying bone with forceps or any other medical instrument other than the syringe of FIG. 12.

The template 70 illustrated in FIG. 9 comprises a clear pliable panel member 71 having openings 75 and 76 formed therethrough. Topographic reference point 71 indicates the facial landmark consisting of the left temple 18 (FIG. 1). Topographic reference point 73 on member 71 indicates the facial landmark consisting of the center point 17 (FIG. 1) of the chin on the face of an individual. The center point 17 lies on the symphysis or median line of the skull. Topographic reference point 74 indicates the facial landmark consisting of the right temple on the face of an individual. The topographic reference points inscribed on template 70 can correspond to any desired facial landmark including the orbital rim of an eye, the tragus of the ear, etc. Each opening 75, 76 indicates an area, for example the upper check, in which a surgeon intends to augment the underlying bone. An opening 75 can have any desired shape and dimension and be formed at any desired location on a template 70. Although template 70 can be formed in flat or arcuate rigid shapes, template 70 is preferably pliable and can, as indicated by dashed lines 77, be bent. In use, template 70 is placed adjacent and bent around the face of a patient such that point 73 is adjacent and in registration with centerpoint 71, such that point 71 is adjacent and in registration with the left temple 18, and such that point 74 is adjacent and in registration with the right temple (not visible in FIG. 1). The surgeon then utilizes a marker to draw on the patient's face a line corresponding to the peripheral edge of opening 75 and or 76. The template 70 is then removed from the face. The surgeon utilizes the line drawn on the patient's face to determine whether bone augmentation material is being inserted at the proper location intermediate facial tissue and underlying bone.

The template 70 is particularly advantageous because it assists a surgeon in symmetrically augmenting equivalent areas on opposite sides of the face. After, for example, the high cheekbone area on the right side of the face of a patient has been augmented, it is sometimes difficult to augment the same equivalent high cheekbone area on the left side of the face. It is difficult for a surgeon to closely examine simultaneously both sides of a patient's face. Template 70 enables a surgeon to mark with some precision two corresponding areas each on an opposite side of a patient's face.

More particularly, in use of the method of the invention, an intraoral incision is made at the point 24 or another point at the front of the upper jaw of the mouth at which the upper lip is attached to or adjacent the gums above the upper central incisors, the upper lateral incisors, the canines, or the first premolars. The incision is typically in the range of about one-fourth to one inch long, and is preferably about three-eighths of an inch long. If bone on the lower jaw is being augmented, then the incision is made at the point 19 or another point at the front of the mouth at which the lower lip is attached to or adjacent the gums below the lower central incisors, the lower lateral incisors, the canines, or the first premolars. After the incision is made at point 24, a scalpel or other sharp medical instrument is inserted through the incision and used to separate facial tissue from underlying bone along a path of travel directed toward a selected treatment area or portion of the face, say the zygomatic bone 20, which the surgeon intends to augment. As appreciated by those of skill in the art, a surgeon can augment bone areas on the face other than areas 16, 20, 21, 22, and 23. Edge 85 on instrument 83 can be used to separate facial tissue from underlying bone. The surgeon also separates facial tissue from underlying bone in the portion of the face which the surgeon intends to augment. After facial tissue is separated from underlying bone, bone augmentation material is inserted adjacent bone in the selected treatment area of the face. The inserted bone augmentation material is generally mediate facial tissue and bone, although some minor amounts of soft facial tissue may remain attached to the bone. The syringe assembly of FIG. 8 can be utilized to inject bone augmentation material intermediate, for example, facial tissue and the underlying zygomatic bone. Housing 61 of syringe 60 is bent into an appropriate arcuate shape and is inserted through the incision until end 66 is positioned intermediate the zygomatic bone 20 and adjacent facial tissue. Plunger 63 is depressed in the direction of arrow C to eject preloaded bone augmentation material from end 66. If desired, a containment pocket 25, 27 is placed intermediate facial tissue and the underlying zygomatic bone 20 before syringe assembly 60 is used to eject bone augmentation material. When a pocket or integument 25 (or 27) is first placed intermediate facial tissue and bone 20, end 66 of assembly 60 is positioned such that bone augmentation material is ejected into pocket 25 (or 27) in the manner indicated by arrow 26 (or 31) in FIG. 2 (or FIG. 3). The pocket 25 preferably, but not necessarily, is long enough to extend out through the incision after the pocket is placed in the desired position intermediate facial tissue and underlying bone. When pocket 25 extends out through the incision, removing and inserting a syringe or other medical instrument in to and out of pocket 25 is a straightforward matter. After filling of the pocket 25 with bone augmentation material is completed, the excess length of pocket 25 is trimmed off, and the open end of the pocket closest to the incision is folded over and, if desired, sutured closed. Bone augmentation material can also be loaded into a pocket 25, 27 before the pocket is inserted through the incision to a position intermediate facial tissue and bone 20.

After a pocket 25 is positioned mediate facial tissue and underlying bone one or more bullets or piece of collagen or other resorbable material can be inserted beneath the pocket to help prevent the pocket 25 from sliding downwardly or migrating from its desired position between facial tissue and underlying bone. The pocket can be sutured or otherwise secured to facial tissue or adjacent bone.

Once bone augmentation material is injected or positioned adjacent bone 20, mediate portion 36 and end 37 of instrument 32 are inserted through the incision such that tip 38 is positioned adjacent bone 20 such that tip 38 can be used to pack or displace the bone augmentation material. The bone augmentation material can be a dry powder, be a malleable mixture of hydroxyapatite powder and high molecular weight or low molecular weight dextran, be a mixture of hydroxyapatite powder and a plasma expander (starch solution), or can take any other form. The weight percent of hydroxyapatite powder and dextran, plasma expander, etc. can vary as desired, but it is often preferred, however, that the bone augmentation material be malleable to facilitate the shaping of the material with tip 38 of instrument 32 or with the tips of any of instruments illustrated in FIGS. 5A, 6A, and 7A. By way of example, and not limitation, a mixture of hydroxyapatite and dextran can be used which includes about thirty to fifty weight percent dextran. When the hydroxyapatite or other bone augmentation material is a malleable mass which tends to hold together, this reduces the likelihood that the augmentation material will migrate once it is deposited intermediate facial tissue (or other tissue) and underlying bone. Consequently, such a malleable mass of material may not, in use, require a pocket 25 or other containment system.

The use of dextran in conjunction with hydroxyapatite or other powders is important in the practice of the invention because it enables a malleable plastic syringe housing 61 to be used in storing and/or dispensing bone augmentation material. Attempting to dispense powder from a pliable plastic syringe is difficult, because the powder frictionally engages the plastic. The use of dextran in combination with hydroxyapatite produces a composition which can be readily dispensed from housing 61 using plunger 63. Further, dextran is resorbable.

After the bone augmentation material has been appropriately shaped, the intraoral incision is sutured closed and the incision is permitted to heal. The portions of facial tissue which were separated from underlying bone grow back to the bone. The bone augmentation material preferably is such that it hardens and sets over time and, as is the case with hydroxyapatite, that it becomes attached to the existing bone structure because the bone structure grows into or around the bone augmentation material. Further, the containment pocket 25, 27 is preferably formed of collagen or another material that is dissolved and/or resorbed by the body such that after a suitable period of time all that remains is the bone augmentation material.

Hydroxyapatite is a crystalline substance containing calcium and phosphorus and is found in certain rocks. It is the basic constituent of bone. The hydroxyapatite composition used as a bone augmentation material can, as noted, simply comprise a dry hydroxyapatite powder. The hydroxyapatite is, however, normally mixed with a liquid substance to form a slurry or more malleable composition which is more readily packed and which remains in fixed position better than dry hydroxyapatite powder. Hydroxyapatite powder can be mixed with water, plaster, collagen, dextran, epinephrine, or some other desirable material. The hydroxyapatite can be obtained from natural mineral sources, from ground bone, etc. Materials other than hydroxyapatite compositions can be used as bone augmentation material. Such other materials can include organic and inorganic matrices and/or combinations thereof. These matrices can be porous, non-porous, active and/or resorbable matrices, or totally inert. For example, coral and coral analogs, polymethyl methacrylate, polyethylene, PTFE (polytetrafluroethylene), polysufone, polymers, polyethylene glycols, osteomin (bone ash), autogenous bone, freeze dried demineralized bone, resorbable and non-resorbable hydroxyapatite, xenographs (bovine), miniscrews, allografts, composites, polyethylene glycol propionaldehyde, HAPSET, or the patient's own bone can be utilized.

In another embodiment of the invention, bone augmentation material is dispensed adjacent underlying bone and is covered with a layer of GORTEX or another pliable piece of material which prevents overlying epithelial or other soft tissue from growing into the bone augmentation material. The GORTEX is then covered with a containment mesh which can include hooks or loops 92, 94, 99 attached to the containment mesh. The overlying facial tissue is then pressed against the containment mesh to press the hooks 92, 94, 99 into the tissue and hold the tissue in place against the containment mesh. If the containment mesh is secured in place to the bone, then the containment mesh acts as an anchor and maintains the facial tissue in place. The facial tissue can also be sutured back together along an incision lines to insure that the facial tissue is secured in place over underlying bone.

There is a common need in reconstructive surgery like plastic surgery or dental surgery to supply supplemental living tissue. Living epithelial or other soft tissue which can be transplanted to a desired site in a patient is not easily obtainable since cadavers ordinarily cannot supply living material and the use of animal tissue is not accepted. Living hard tissue, i.e., bone, is difficult to remove from cadavers or from the patient's body. Consequently, instead of living tissue, surgeons ordinarily use a variety of natural and synthetic tissue augmentation materials. Such augmentation materials include various inorganic materials like ceramics and metals and organic materials like polymers. Such inorganic and organic augmentation materials usually suffer from at least one of several disadvantages. First, the organic or inorganic tissue augmentation material may be inert and remain in the reconstruction area indefinitely and interfere with the restoration of living tissue by natural growth in the reconstruction area. Second, the tissue augmentation material can, as earlier described, migrate into other tissue areas. Third, the tissue augmentation material can permit unwanted tissue (i.e., epithelial tissue) from outside the reconstruction area to penetrate into the augmentation material and interfere with the regeneration of desired living tissue (i.e., bone). In order to overcome some or all of the preceding disadvantages, several approaches are possible in accordance with the invention. For augmentation materials that essentially remain intact at the reconstruction area, biodegradable scaffolds can offer superior performance characteristics. For tissue augmentation materials that migrate, a variety of degradable or nondegradable containment systems can be created to prevent such migration. For tissue augmentation materials that cannot, standing alone, provide an effective barrier against ingrowth by unwanted tissue, materials providing controlled permeability and/or porosity would be desirable. For example, a tissue augmentation materials can be provided with a permeability or porosity which enhances the ingress/egress of desired biochemicals or cells (e.g. bone cells) while minimizing the ingress and egress of unwanted biochemical or cells (e.g. epithelial cells). It is also possible to use combinations of these materials that can serve as a barrier and/or tissue augmentation agent to obtain two or more desired properties. For example, a tissue augmentation material can be created from a single material or a combination of two or more materials that have a variety of desirable characteristics. Example of desirable properties for tissue augmentation materials created from a single material include: inert and nonporous, inert but porous, bioactive but nonporous, or bioactive and porous. A bioactive material is one that can intentionally controls one or more biological or material process and/or material-host response, where the host comprises a patient's body or portion thereof. Also, it may be desirable to have combinations of two or more materials to provide a tissue augmentation material created in a composite fashion and having additional characteristics such as inertness, bioactivity, and porosity that are, when the reconstructive material is used in the body, controlled by spatial, temporal, physicochemical, energy, and other parameters.

One containment system that can be used to minimize or prevent the migration of hydroxyapatite is a barrier consisting of a porous, biodegradable pocket 25 or other similar containment system comprised of a natural, porous biomaterial like collagen. As used herein, a barrier indicates a material that is able to control the flow of matter and/or energy in a deliberate way by spatial, temporal, physicochemical or other physical means alone or in combination. The containment system can also be used to contain and enhance the delivery of nutrients and other components that enhance the tissue reconstruction process. Another feature of the containment system is that it may be created in vitro prior to the dispensing of tissue augmentation material or in vivo during the dispensing of the tissue augmentation material.

A variety of collagen materials can be used alone and in combination (Types 1 to 12) to form a containment pocket 25 or other structure which may have useful features of controlled degradation and porosity for tissue reconstruction. Other known naturally occurring materials such as biopolymers, cross-linked protein scaffolds, and gels can be used alone or in combination with each other or with any other material to form a containment system for hydroxyapatite or other tissue augmentation materials. A containment pocket 25 or other structure can be formed with synthetic organic materials such as polymers or plastics, with natural inorganic materials (e.g., hydroxyapatite and other ceramics), with organic materials (e.g., biopolymers), or with synthetic inorganic materials.

Possible polymers usable in a pocket 25 or other containment structure constructed in accordance with the invention include, without limitation, poly(Amides), poly(Esters), poly(Orthoesters), poly(Anhydrides), poly(Ureas), poly(Alkyl 2-Cyanocrylates), poly(Dihydropyrans), poly(Acetals), poly(Phosphazenes), and poly(Dioxinones). Each of the foregoing polymers is biodegradable in natural systems by undergoing a hydrolytic and/or enzymatic breakdown and, as such, are capable of providing biodegradable matrices, scaffolds and other useful structures of a containment structure. Examples of biodegradable polyamides includes glutamic acid, glutamic acid/leucine, nylon, glutamic acid/ethyl glutamate, hydroxyalkyl-L-glutamine, and collagen. Examples of biodegradable polyesters include D, L latic acid, glycolic acid/lactic acid, L-latic acid, caprolactone/D,L lactic acid, diglycolic acid/transcyclohexanedimethanol, and polyesterhydrogels.

In one embodiment of the invention, hydroxyapatite is mixed with a biodegradable polymer, with or without a growth agent impregnated therein, to provide a composition which resists penetration by epithelial tissues but which promotes growth of adjacent bones structure.

In a further embodiment of the invention, a pocket 25 or other containment structure is fabricated from a microporous material containing a drug or other agent in its pores which promotes the growth of living tissue. The pore sizes can be in the range of 25 to 400 microns, or can have any desired size.

In another embodiment of the invention, hydroxyapatite or another tissue augmentation material is mixed with a material to produce a mixture which hardens and which resists penetration by epithelial tissues but which promotes growth of adjacent bones structure.

In a further embodiment of the invention, a pocket 25 or other containment structure is fabricated from a microporous material containing a drug or other agent in its pores which promotes the growth of living tissue. The pore sizes can be in the range of 25 to 400 microns, or can have any desired size.

In another embodiment of the invention, hydroxyapatite or another tissue augmentation material is mixed with a material to produce a mixture which hardens and sets after being dispensed at a desired location intermediate the facial tissue and underlying bone. UV light can be delivered by fiber optic means to the location at which the augmentation material is dispensed intermediate facial tissue and underlying bone. The UV promotes the hardening or setting up of certain materials.

In still another embodiment of the invention, a volume of tissue augmentation material is provided with a coating which resists migration from the tissue augmentation material of tissue augmentation drugs or other materials. The coating can be biodegradable and break down over time.

Figure 13:
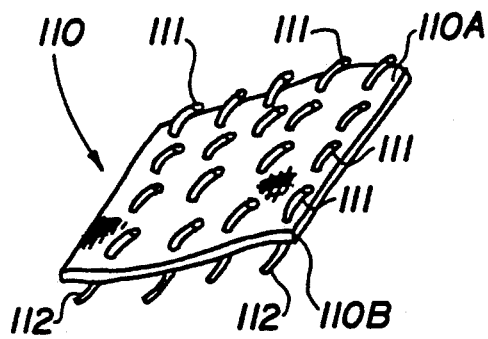
FIG. 13 is a perspective view illustrating a quill member utilized to anchor a piece of material in position.

The quill member illustrated in FIG. 13 includes a piece of material 110 having a front surface 110A and a back surface 110B generally parallel and opposed to front surface 110A. Pins 111 are attached to material 110 and extend outwardly from the front surface 110A. Pins 112 are attached to material 110 and extend outwardly from the back surface 110B. While pins 111 can be perpendicular or at any angle with respect to surface 110A and pins 112 can be perpendicular or at any angle with respect to surface 110B, in FIG. 13 pins 111 and 112 are canted with respect to surfaces 110A and 110B, respectively. Further, pins 111 are canted in a direction opposite that of pins 112. The canting of pins 111 and 112 in opposite directions is important in the utilization of the invention depicted in FIGS. 14A and 14B.

Figure 14A:
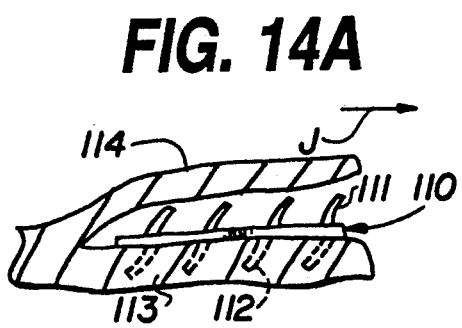
FIG. 14A is a side view illustrating the mode of use of the quill member of FIG. 13.
Figure 14B:
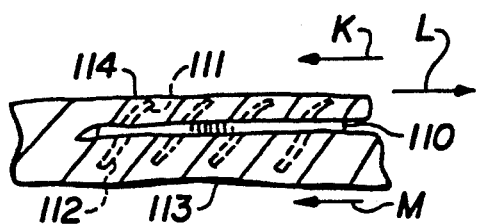
FIG. 14B is a side view further illustrating the mode of use of the quill member of FIG. 13.

In FIG. 14A, the quill member of FIG. 13 has been inserted intermediate the flap 114 of skin or other tissue and pressed against underlying tissue 113 such that pins 112 have pierced and extend into tissue 113 and such that the bottom surface 110B contacts tissue 113. After the quill member is positioned in the manner illustrated in FIG. 14A, the flap 114 is gently pulled or stretched in direction of arrow J and is downwardly pressed against the quill member to the position shown in FIG. 14B such that surface 110A contacts flap 114 and pins 111 pierce and extend into flap 114. In FIG. 14B, resilient flap 114 gently pulls against pins 111 in the direction of arrow K. The canting of pins 111 in the direction of arrow L helps to offset the pull of flap 114 in the direction of arrow K. Similarly, the canting of pins 112 in the direction of arrow M helps to offset the tendency of the quill member to be displaced in the direction of arrow M due to the pull of flap 114 in the direction of arrow K.

Figure 15:
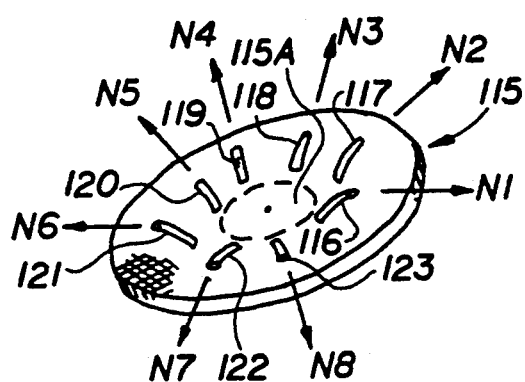
FIG. 15 is a perspective view illustrating an alternate embodiment of the quill member of the invention.
Figure 16:
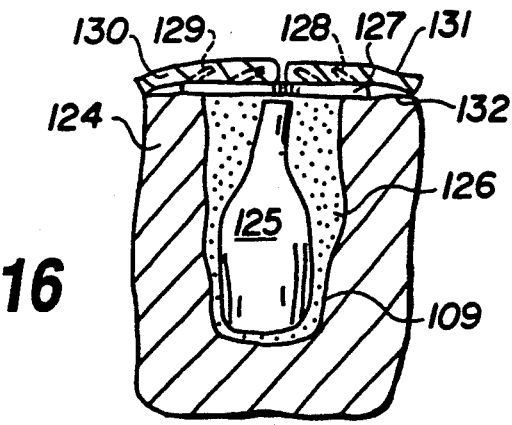
FIG. 16 is a side elevation view illustrating the application in a dental implant procedure of a quill member constructed in accordance with the principles of the invention.
Figure 18:
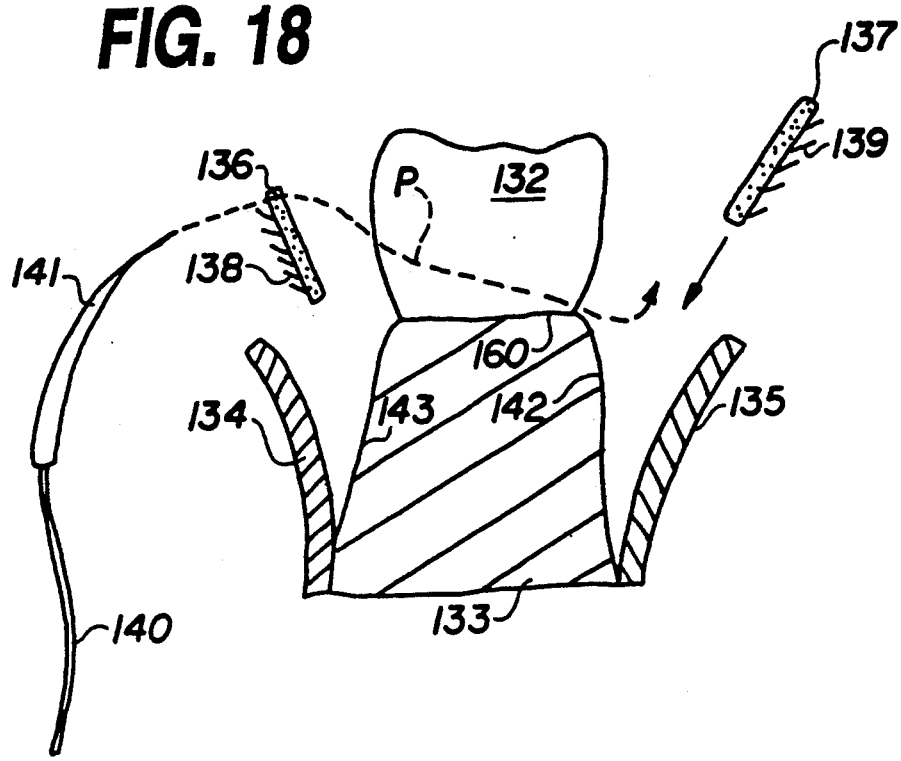
FIG. 18 is a partial side section view of the alveolar bone ridge illustrating a method for coronally positioning the gingiva covering the alveolar bone ridge.
Figure 19:
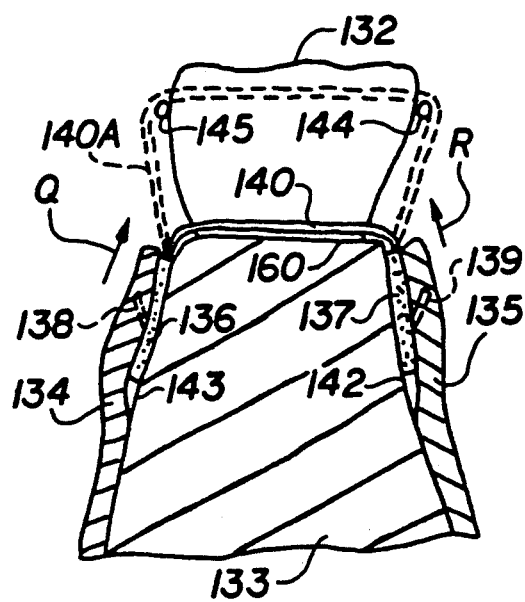
FIG. 19 is a partial side section view of the alveolar bone ridge of FIG. 18 further illustrating the method for coronally positioning the gingiva.
Figure 20:
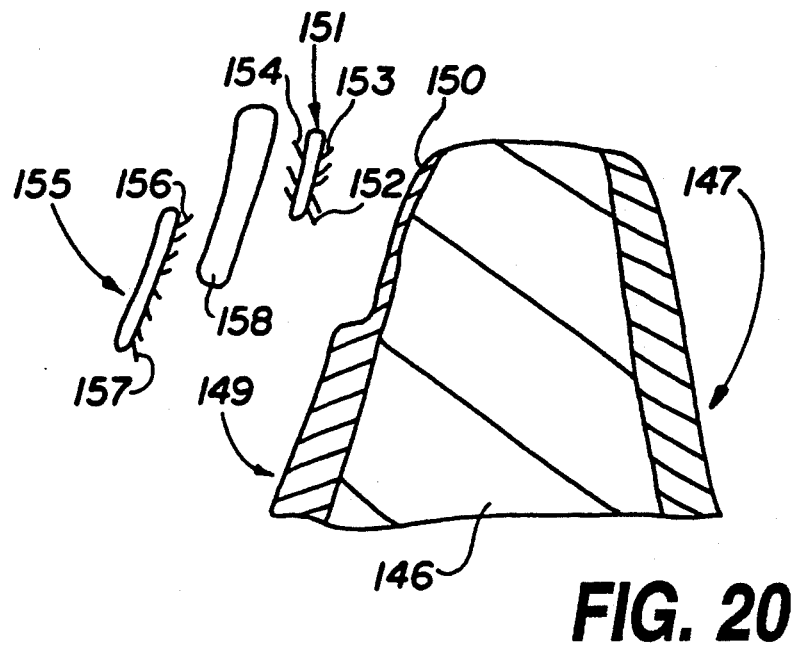
FIG. 20 is a partial side section view of the alveolar bone ridge illustrating a method for grafting pink gingiva adjacent the ridge; and, FIG. 21 is a partial side section view of the alveolar bone ridge of FIG. 20 further illustrating the method for grafting pink gingiva adjacent the ridge.
Figure 21:
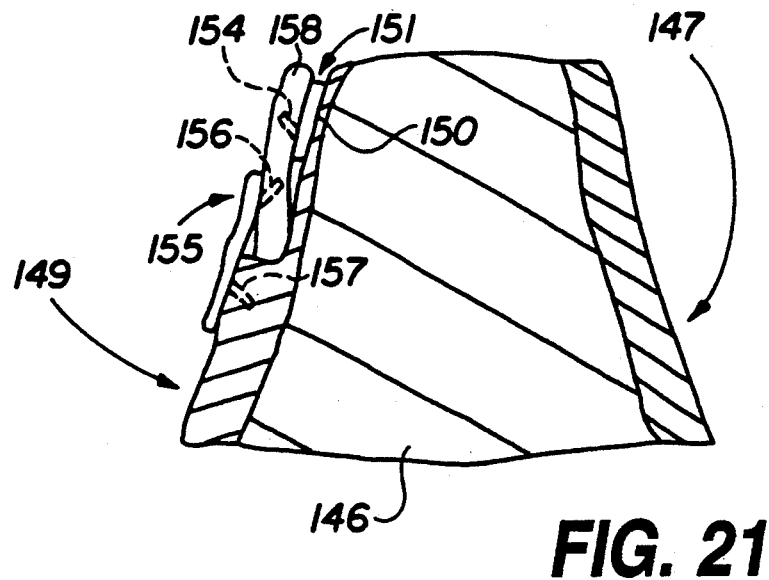

While pins 111 and 112 in FIGS. 13 and 14, pins 116 to 123 in FIG. 15, pins 128 and 192 in FIG. 16, pins 138 and 139 in FIGS. 18 and 19, pins 152 to 154 and 156 and 157 in FIGS. 20 and 21, are each illustrated as having a generally cylindrical shape, it is understood that such pins can take on any shape and dimension, or orientation, to facilitate the piercing and engaging of body tissue. The pins can, for example but not by way of limitation, include barbs or sharp points, be triangular or square in cross-section, be straight, be arcuate, be perpendicular to a surface 110A, be canted with respect to a surface 110B, etc. Further, the pins 111 and 112 in FIGS. 13 and 14, pins 116 to 123 in FIG. 15, pins 128 and 129 in FIG. 16, pins 138 and 139 in FIGS. 18 and 19, pins 152 to 154 and 156 and 157 in FIGS. 20 and 21, can, if desired, be used on a containment pocket 25, 27. For example, using a plurality of radially oriented pins 116 to 123 in an arrangement similar to that of FIG. 15 might facilitate the anchoring of a containment pocket 25, 27 in position against a piece of tissue.

Figure 17:
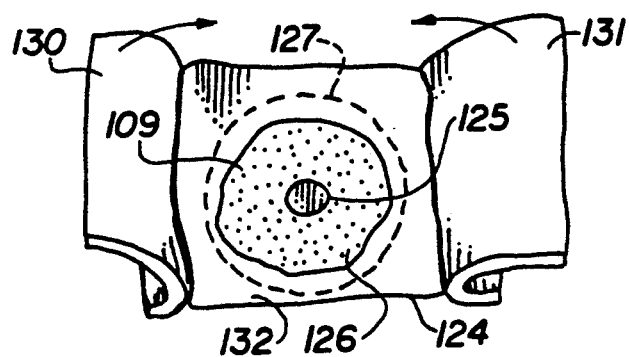
FIG. 17 is a top view illustrating the alveolar bone structure and dental implant of FIG. 16.

Material 110 in FIG. 13, material 115 in FIG. 15, material 127 in FIGS. 16 and 17, material 136 in FIGS. 18 and 19, and material 151 and 155 in FIGS. 20 and 21, can be pliable, semi-pliable, or rigid; can be solid, semi-porous, or porous; can in whole or in part be biodegradable by bodily fluids or tissues; can in whole or in part be biocompatible with bodily tissues or fluids; can be comprised of a single or multiple layers; and, can be woven or non-woven. For example, but not by way of limitation, in one embodiment of the invention material 110 is a biodegradable mesh which permits tissue to grow through the mesh and which is broken down by the body over time. Pins 111, 112, etc. can also be fabricated from biodegradable material, such as stiff suture material.

FIG. 15 illustrates a quill member including pins 116 to 123 connected to and extending radially outwardly from the circular piece of material 115. Pins 116 to 123 are canted radially outwardly in the directions indicated by arrow N1, N2, N3, N4, N5, N6, N7, and N8, respectively. In contrast to the orientation of pins 116 to 123 shown in FIG. 15, pins 116 to 123 can be canted radially inwardly in directions opposite that of arrows N1 to N8. If, for example, pin 123 is canted radially inwardly, it is canted in the direction generally indicated by arrow N4. If pin 119 is canted radially inwardly, it is canted in the direction generally indicated by arrow N8. When a pin 116 to 123 is canted radially inwardly, it is canted toward central area 115A. When a pin 116 to 123 is canted radially outwardly, it is canted away from area 115A. Pins 116 to 123 circumscribe central open area 115A of the quill member. It is sometimes desirable to provide an open area in a quill member against which body tissue may rub without contacting pins 116 to 123 and without being injured. For example, the quill member of FIG. 15 can be placed over alveolar bone in the mouth and pins 116 to 123 covered with gum tissue such that area 115A is not covered by gum tissue and the tongue brushes against open area 115A and is not contacted by the pins.

In FIG. 16, wine bottle-shaped dental implant 125 is packed in opening 109 by a hydroxyapatite composition 126. Opening 109 is drilled or otherwise formed in alveolar bone 124. A quill member including circular material panel 127 is placed on the surface 132 of bone 124 to maintain gum tissue flaps 130 and 131 in place over implant 125. Flap 130 is gently pulled toward flap 131 and pressed against pins 129 to secure flap 130 in the position shown in FIG. 16. Flap 131 is gently pulled toward flap 130 and is pressed against pins 128 to secure flap 131 in the position shown in FIG. 16. Since flap 131 tends to pull away from flap 130, and vice-versa, the quill member facilitates maintenance of the flaps 130 and 131 in the position illustrated in FIG. 16. Pins 128 and 129 are attached to and extend outwardly away from material panel 127.

FIG. 17 is a top view illustrating the flaps 130 and 131, implant 125, hydroxyapatite composition 126, opening 109, and surface 132 just prior to the placement of the circular quill member in the position shown in FIG. 16 and prior to displacement of flaps 130 and 131 against pins 129 and 128. The shape and dimension of the quill member utilized in FIG. 16 is similar to that of the quill member of FIG. 15, except that the pins in the quill member of FIG. 16 point radially inwardly.

With age or after the extraction of a tooth, gum tissue tends to recede from the top or peak of the alveolar bone ridge anchoring the teeth in a mouth. It would be highly desirable to be able to extend or stretch the gingiva upwardly back toward the top or peak of the alveolar bone ridge. Such a coronal repositioning of the gingiva is, however, difficult to accomplish. A method for facilitating the coronal repositioning of the gingiva in accordance with the invention is illustrated in FIGS. 18 and 19.

In FIG. 18, flaps 134 and 135 of the gingiva are peeled away from the inside 143 and outside 142 surfaces, respectively, of the alveolar bone ridge 133 anchoring tooth 132. One quill member including a rectangular panel of material 136 and canted pins 138 is positioned intermediate flap 134 and inside surface 143 in the manner illustrated in FIG. 19, and flap 134 is pressed against pins 138 such that the upper portion of flap 134 is held against material 136. The panel of material 136 can have any desired shape and dimension, as can the panels of material 110, 115, 127, 155, 151, and 137. Another quill member including a rectangular panel of material 137 and canted pins 139 is positioned intermediate flap 135 and the outside surface 142 in the manner illustrated in FIG. 19, and flap 135 is pressed against pins 139 such that the upper portion of flap 135 is held against material 137. A needle 141 or other means is used to attach a length of suture 140 to material 136 and 137 such that material 136 and flap 134 are pulled upwardly in the direction of arrow Q and material 137 and flap 135 are pulled upwardly in the direction of arrow R. Suture 140 extends from material 136 over the peak or top 160 of bone ridge 133 to material 137. If the gum material (not shown) covering the top of ridge 133 is too thick or too soft, then suture 140 can be held in position over the peak of ridge 133 by extending suture 140 over a tooth or over support wires 144, 145 or other support structures anchored to tooth 132 or other teeth or anchored to ridge 133. In FIG. 19, wires 144 and 145 are perpendicular to the sheet of paper of the drawing and run along the side of tooth 132 generally parallel to the peak 160 and the gum line at the bottom of the tooth 132. Dashed lines 140A indicate the manner in which a piece of suture can extend over peak 160 from material 136 to material 137 by passing over support wires 144 and 145. Suture 140 can comprise a piece of suture, wire, string, or other material which can perform the above described functions of pulling materials 136 and 137 upwardly in the direction of arrows Q and R. In FIG. 19, the upwardly canted pins 138 and 139 help prevent flaps 134 and 135 from sliding off of pins 138 and 139, respectively. Pins 138 and 139 can, instead of being upwardly canted, be downwardly canted or be perpendicular to the panels 136, 137 of material and be provided with hooks to engage and hold gingival flaps 134 and 135 in position.

The advantage of the coronal displacement method illustrated in FIGS. 18 and 19 is that the quill members securely engage gingival flaps 134 and 135 and permit the flaps 134 and 135 to be gradually coronally stretched toward peaks 160 of ridge 133.

The pink gum tissue at the base of each tooth in the mouth of a human being functions to adhere to and hold the tooth in place. After an individual loses a tooth and does not promptly replace the tooth using an implant and artificial tooth, the body permits the pink gum tissue to wither away. If, after the pink gum tissue has withered away, the individual wishes to having an implant and artificial tooth placed at the location of the old tooth, it is desirable to attempt to replace the pink gum tissue with a graft from the palate. The problem encountered in such grafts is that the graft will not stay in position at the graft site, tends to move and separate from the graft site, and to die. The invention provides an improved method for insuring that the graft maintains it position at the donor site. The improved method is illustrated in FIGS. 20 and 21.

FIG. 20 illustrates the alveolar bone ridge 146 in the mouth of an individual. A layer of gum tissue 147 extends over the inside of ridge 146. A layer of gum tissue 149 extends over the outside of ridge 146. A donor site is prepared by cutting away a rectangular piece of the outer layers of gum tissue 149 such that the underlying periosteal tissue 150 remains. A rectangular piece of pink graft tissue 158 is harvested from the individual's palate and is anchored in place over tissue 150 using a pair of quill members. One of the quill members includes a rectangular piece of material 151 having pins 152, 153, and 154 attached and extending outwardly from material 151. Material 151 is a porous mesh which will permit blood and other bodily fluids to travel from tissue 150, through material 151, and to tissue 158 to help keep tissue 158 alive. Pins 154 are each canted in the same direction. Pins 153 are each canted in the same direction. Pins 152 are each canted in the same direction and are canted away from pins 153. The other quill member includes a rectangular piece of material 155 having pins 156 and 157. Pins 156 are each canted in the same direction. Pins 157 are each canted in the same direction and are canted away from pins 156.

FIG. 21 illustrates graft tissue 158 after it has been anchored on the periosteal tissue 150 using the quill members. One quill member is positioned intermediate tissue 158 and periosteal tissue 150. Pins 152 and 153 (not visible in FIG. 21) extend outwardly from material 151 into periosteal tissue 150 and pierce and engage the tissue 150. Pins 154 extend outwardly from material 151 into tissue 158 and pierce and engage tissue 158. The material 155 of the other quill member is positioned against and contacts the outer surface of tissue 158 and of adjacent gum tissue 149. Pins 156 extend outwardly from material 155 and into graft tissue 158 and pierce and engage tissue 158. Pins 157 extend outwardly from material 151 into tissue 149 and pierce and engage tissue 149. Materials 151 and 155 and pins 156, 157, 152, 153, and 154 are all fabricated from biodegradable material. If desired, only the quill member including material 155 need be used to anchor graft tissue 158 in place; or, only the quill member including material 151 need be utilized. The quill members of FIGS. 20 and 21 are believed to do an improved job of anchoring tissue 158 in position at the donor site because the forces necessary to hold tissue 158 in place are distributed among many pins 156, 157, 152, 153, and 154 and are distributed over a large surface area in graft tissue 158. The density, size, and spacing of pins 156, 157, 152, 153, and 154, as well as the orientation and shape of the pins, can be varied as desired. Some of the pins may be longer than others. One pin 156 may have a length, shape, etc. different from another pin 156 or 157. A quill member material 155 or pin 156 can be porous, or can include pharmaceuticals to facilitate healing of tissue 158 to the donor site.

As would be appreciated by those of skill in the art, the quill members of FIGS. 13, 15, 16, 18, and 20 can be utilized at various locations throughout an individual's body to engage and help secure tissue in a selected position against bone or against other tissue. The size and shape of the quill member(s) would depend on the tissue involved. In FIG. 21, a portion of tissue 158 directly contacts the periosteal tissue 150 and does not contact material 151. In some instances it might be desirable to utilize spaced apart small pieces of quill material to connect an overlying layer of tissue 158 to another underlying layer of tissue 150 so that portions of the overlying layer will directly contact the underlying layer. In other instances, it might be desirable not to have an quill members intermediate a pair of layers of tissue 150, 158 and to instead anchor one of the layers of tissue 158 by connecting it to a third adjacent layer 149 of tissue in the manner accomplished by the pins attached to material 155 in FIG. 21.

As would be appreciated by those of skill in the art, a flap of tissue can, prior to being secured in a desired position by a quill member, still be partially attached to surrounding tissue like flap 114 in FIG. 14A or can be completely severed from the body like the flap of tissue 158 in FIGS. 20 and 21.

Having described our invention in such terms as to enable those skilled in the art to understand and practice it, and having identified the presently preferred embodiments thereof, we claim:

1. A method for coronally repositioning the gingiva, comprising the steps of
   (a) separating a first gingiva flap from the bone on the inside an alveolar bone ridge supporting teeth in the mouth, said ridge having a peak;
   (b) separating a second gingiva flap from the bone on the outside of said alveolar bone ridge, said second flap generally being opposed to said first flap;
   (c) positioning a first quill member intermediate said first flap and said bone ridge, said quill member including a pliable panel of material having a back and a front surface and including a plurality of gingiva piercing pins attached to said panel and outwardly projecting from said front surface, said quill member being positioned intermediate said first flap and said bone ridge such that said back is against said bone ridge;

(c) pressing said first flap against said quill member such that said pins pierce and engage said first flap;

(d) positioning a second quill member intermediate said second flap and said bone ridge, said second quill member including a pliable panel of material having a back and a front surface and including a plurality of gingiva piercing pins attached to said second quill member and outwardly projecting from said front surface of said second quill member, said second quill member being positioned intermediate said second flap and said bone ridge such that said back of said second quill member is against said bone ridge;

(e) pressing said second flap against said second quill member such that said pins of said second quill member pierce and engage said second flap;

(f) coronally pulling said first flap and second flap toward said peak of said bone ridge by interconnecting said first and second quill members with a length of suture which extends over said peak and upwardly pulls said quill members toward said peak.

2. A method for grafting pink gum tissue to gum tissue adjacent alveolar bone, comprising the steps of (a) preparing a donor site by removing gum tissue to expose underlying periosteal tissue;

(b) harvesting from the palate a piece of donor tissue shaped to be placed on the donor site;

(c) placing said donor tissue on the periosteal tissue at said donor site; and, (d) anchoring said donor tissue to the gum tissue adjacent said donor tissue by pressing a quill member against said donor tissue and said adjacent gum tissue, said quill member including a pliable piece of material and a plurality of pins attached to and extending outwardly from said piece of material, said pins piercing and engaging said donor tissue and said adjacent gum tissue when said quill member is pressed against said donor tissue and said adjacent gum tissue.

3. A method for securing a second layer of soft tissue in a body in a selected position with respect to a first layer of soft tissue in the body, comprising the steps of (a) pressing a quill member against said first layer of soft tissue, said quill member including a piece of material having a front side and a back side spaced apart from and opposing said front side, a plurality of pins attached to and extending outwardly from said front side of said material and shaped and dimensioned to pierce said first layer of soft tissue, and a plurality of pins extending outwardly from said back side of said material and shaped and dimensioned to pierce said second layer of soft tissue, said pains extending outwardly from said front side piercing said first layer of soft tissue when said quill member is pressed against said first layer; and, (b) pressing said second layer of soft tissue toward said piece of material and against said plurality of pins extending outwardly from said back side of said material to pierce said second layer with said pins extending from said back side of said material such that said second layer extends over said first layer.

4. A method for securing a piece of material to soft tissue in a body, said piece of material (110) having a front side and a back side and a plurality of soft tissue piercing pins (111) attached to said piece of material and extending outwardly from said front side such that said pins (111) are canted in a selected direction (J) with respect to said front side, said method including the steps of (a) pressing said tissue piercing pins and said soft tissue together such that said pins pierce said soft tissue and said front side of said piece of material contacts said soft tissue; and, (b) tensioning said soft tissue to force portions of said soft tissue toward said canted pins in a direction (K) opposite said selected direction (J).

5. A method for securing a second layer of soft tissue in a body in a selected position with respect to a first layer of soft tissue in the body, comprising the steps of (a) placing said first layer and said second layer of soft tissue adjacent and side-by-side one another;

(b) interconnecting said first and second layers by pressing a quill member against said first layer and said second layer of soft tissue, said quill member including a piece of material extending from said first layer to said second layer and including a plurality of pins attached to and extending outwardly from said piece of material, said pins piercing and engaging said first and second layers of soft tissue when said quill member is pressed against said first and second layers.

* * * * *